United States Patent [19]
Merten

[11] 3,937,211
[45] Feb. 10, 1976

[54] MULTI-PURPOSE SYRINGE
[75] Inventor: Utz P. Merten, Cologne, Germany
[73] Assignee: Fa. Walter Sarstedt Kunststoff-Spritzgusswerk, Numbrecht, Rommelsdorf, Germany
[22] Filed: Oct. 23, 1973
[21] Appl. No.: 408,568

[30] Foreign Application Priority Data
Oct. 27, 1972 Germany............................ 39445

[52] U.S. Cl............................ 128/2 F; 128/218 P
[51] Int. Cl.²........................ A61B 5/00; A61M 5/00
[58] Field of Search ............ 128/218 R, 218 P, 272, 128/218 M, 218 D, 220, 218 C, 218 PA, 234, 236, 261, 276, DIG. 5, DIG. 28, 2 F, 218 N, 218 OA, 218 F, 215, 235; 222/386; 206/364, 365, 438, 439

[56] References Cited
UNITED STATES PATENTS

| | | | |
|---|---|---|---|
| 1,110,189 | 9/1914 | Dodge................................. | 128/234 |
| 2,183,482 | 12/1939 | Kurkjian ............................. | 128/261 |
| 3,013,557 | 12/1961 | Pallotta......................... | 128/DIG. 5 |
| 3,164,303 | 1/1965 | Trautmann ............... | 128/218 PA X |
| 3,566,859 | 3/1971 | Schwartz ............................. | 128/2 F |
| 3,577,980 | 5/1971 | Cohen ................................. | 128/2 F |
| 3,815,580 | 6/1974 | Oster .................................. | 128/269 |

FOREIGN PATENTS OR APPLICATIONS

| | | | |
|---|---|---|---|
| 112,404 | 12/1968 | Denmark......................... | 128/218 P |
| 44,211 | 8/1888 | Germany......................... | 128/218 P |
| 79,206 | 5/1955 | Denmark......................... | 128/218 P |
| 1,491,834 | 8/1969 | Germany......................... | 128/218 R |

*Primary Examiner*—Robert W. Michell
*Assistant Examiner*—Rick Opitz
*Attorney, Agent, or Firm*—Edward E. Sachs

[57] ABSTRACT

A multi-purpose syringe for extracting a body fluid, storing the fluid and being adapted to be employed as the test vial for centrifugation. The syringe includes a vial and at the forward end a nozzle which is threadedly connected for sealing purposes to a cap which has a spike extending into the passageway through which blood is drawn. A threaded end cover sealingly engages the rearward end of the vial and piston rod protrudes therethrough. The rod has at the forward end a piston head provided with a rearwardly extending sleeve which is placed into sealed locking engagement with the end cover after the specimen has been introduced or drawn into the vial. The combination of the cap at one end and the cover member at the other end provides a complete seal for the container. The piston rod has two portions which can be severed from each other.

8 Claims, 5 Drawing Figures

MULTI-PURPOSE SYRINGE

The present invention relates generally to syringes and, more particularly, to multi-purpose syringes for extracting body fluid, particularly blood specimen, and for storing the specimen within the syringe with the construction of the syringe being such that the same can be placed into a centrifuge for centrifugation of the blood specimen.

The difficulties and dangers encountered in this art are related to the handling of the syringe after the blood specimen or other body fluid has been extracted and is to be forwarded, for instance by mail, to another location for centrifugation. Conventionally, the blood in the vial is transferred to a shipping container which, in turn, is placed into the centrifuge mechanism. The transfer of the specimen from one container to another increases the possibility of contaminating the specimen which can have a distorting influence upon the analysis which is to be made, or, vice versa, the specimen can infect those who come in contact with it.

Additionally, the handling of the syringe filled with a liquid specimen presents problems with respect to proper sealing particularly since, at the present time, throw-away type syringes are very prevalent, and the seals are sometimes not very liquid-tight.

It is therefore the primary object of the present invention to provide a syringe which is constructed to perform the three functions, i.e., to extract the specimen, to store and ship the specimen within the same vial and to permit the vial to be used as a container which can be used for centrifugation.

Both ends of the syringe have liquid-tight integrity and after the specimen has been extracted a portion of the piston rod can be removed so that the container can be shipped or otherwise more readily handled without harm to any of the sealing components and environment.

It is another object of the present invention to provide a syringe in which the rearward end as well as the forward end are provided with double seals to preclude leakage.

It is a still further object of the present invention to provide a syringe of the type described in the preceding paragraph in which the piston rod can be shortened after the extraction of the blood has taken place.

These objects are accomplished and the present invention resides in providing a multi-purpose syringe for extracting blood, storing the blood, serving as a shipping container and being adapted to be placed into a centrifuge. The syringe includes a vial having a forward and a rearward opening in communication with the interior of the vial, a nozzle which encloses the forward opening and provides a passageway thereform and is adapted for receiving a conventional hypodermic needle when the syringe is to be utilized. A cap is detachably mountable on the nozzle for sealingly covering the nozzle and the passageway thereof. An end closure or cover is detachably secured to the rearward end of the vial to sealingly enclose the rear opening and includes a connecting arrangement which extends forwardly into the vial, i.e., in the direction of the nozzle. Finally, the syringe includes a longitudinally extending piston arrangement which projects a rod through the end closure into vial and terminates therein with a piston head. The piston head includes a rearwardly extending connecting arrangement for entering into a sealed mechanically torsional locking arrangement with the connecting arrangement of the end closure.

For a better understanding of the present invention, together with other and further objects thereof, reference is had to the following description taken in connection with the accompanying drawings, and its scope will be pointed out in the appended claims.

Figure 1:
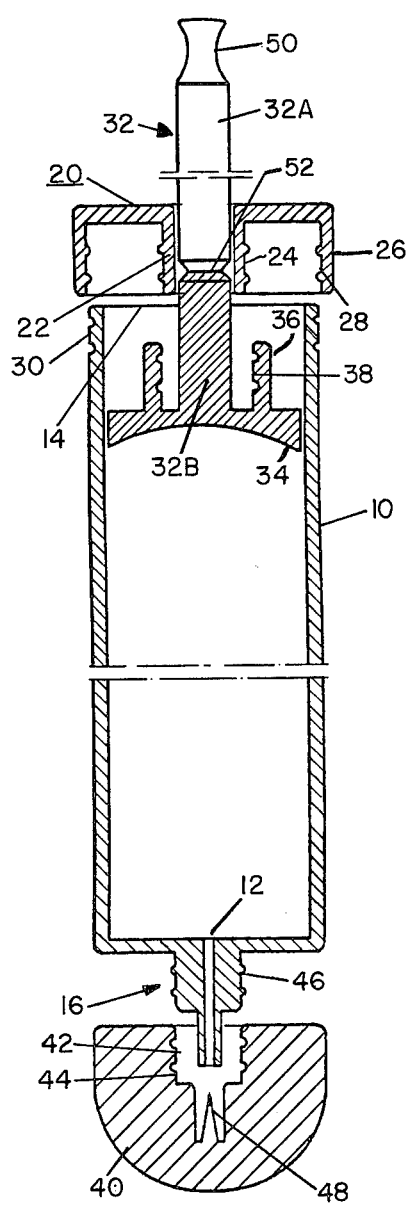
FIG. 1 is a longitudinally extending cross sectional view, in part expanded, of the syringe in accordance with the present invention showing certain elements detached from the vial.

Referring now to the drawings, there is shown a vial 10 comprising an elongated tubular member having a forward opening 12 and a rearward opening 14. The vial can be composed, conventionally, of plastic, glass or other material. Preferably, the vial 10 is constructed of plastic so that there is integrally formed thereon at the forward end a nozzle 16 which has a passageway 18 which extends from and is in direct communication with opening 12. The forward end of the passageway 18 is adapted for receiving a hypodermic needle (not shown) when the syringe is to be used for extracting a body fluid specimen, such as blood. For simplicity, the terms "body fluid specimen" and "blood" have been used interchangeably and no particular limitation is intended when one term or the other is used.

Figure 3:
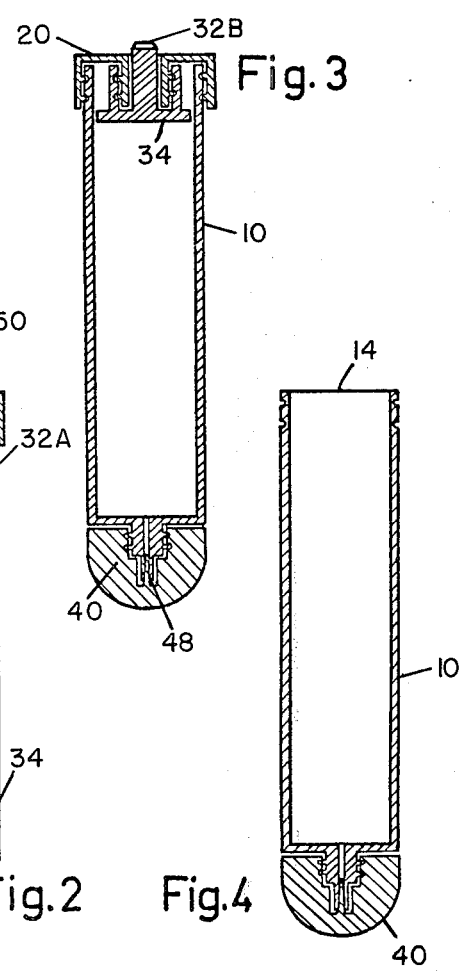
FIG. 3 is a view similar to FIG. 1 showing the vial after portions of the plunger have been removed and both end elements have been placed in situ.
Figure 4:
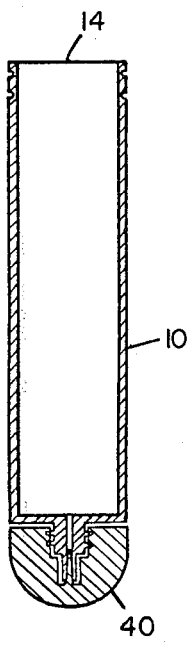
FIG. 4 is again a view similar to FIG. 1, however, showing the vial with the end closure and piston removed and ready for use in a centrifuge.

The rearward end opening 14 is covered by an end closure 20 formed of a double tube wall which is joined together rearwardly with the inner wall 22 having an external thread 24 and the outer wall 26 having an internal thread 28. The end closure 20 is threadedly secured to the vial 10 by means of threads 30 provided externally on the vial 10 at the rearward end thereof. Extending axially through the closure 20 is a plunger or piston rod 32 having rod portions 32A and 32B, the rod portion 32B terminates with a piston head 34 whose radial circumference sealingly engages the inner wall of the vial. The piston head 34 includes, integrally, a tubular sleeve 36 which extends rearwardly from the piston 34 and is provided with an internal thread 38 which is adapted to threadedly engage with the end closure member 20, for sealed locking engagement, as shown in FIG. 3.

After the blood or specimen has been extracted and the hypodermic needle (not shown) has been removed, the forward end of the nozzle 16 is sealed by a cap 40 which is mounted thereon. For this purpose the cap 40 is provided with an internal opening 42 having an inside thread 44 which sealingly engages external thread 46 provided on the outer surface of nozzle 16. In order to ensure that the cap 40 provides a good seal there is additionally provided within the opening 42 a spike or plug 48 which has a pointed end facing the passageway 18 and when the cap 40 is in threaded engagement with the nozzle 16 protrudes into the passageway and significantly seals the same.

Figure 2:
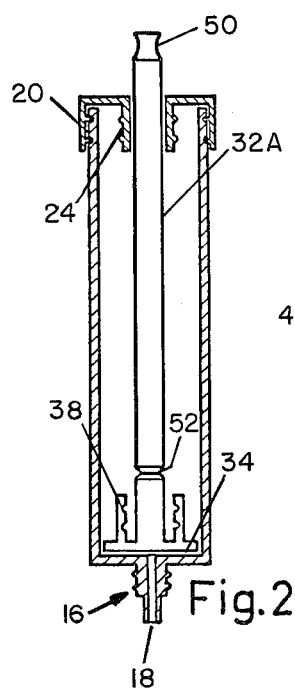
FIG. 2 is a view similar to FIG. 1, however, showing the rearward closure cover in situ and the piston in actuating position.

Referring to FIG. 2, there is shown the syringe in a fully assembled condition prior to securing the hypodermic needle thereto. The rod portion 32A, and more particularly the rearward terminal end thereof, is provided with a grip 50 to pull the rod and piston 32, 34, rearwardly for drawing the specimen. When a sufficient amount of the specimen has been extracted, the piston head is either in a rearward position or is intentionally moved rearward for threaded engagement with the external thread 24 of closure 20 and internal thread of sleeve 36 which establishes a tight locking and sealing engagement between the two members 20 and 34.

Thereafter, the portion 32A and 32B of rod 32 may be severed from each other in order to eliminate the portion 32A from protruding outwardly beyond the end closure member 20 to any significant degree.

To accomplish this, the rod 32 is constructed in such a manner that the portion 32A is significantly longer than portion 32B and the juncture 52 between the two portions is radially reduced so that the portion 32A can be manually broken off, without any difficulty.

Figure 1A:
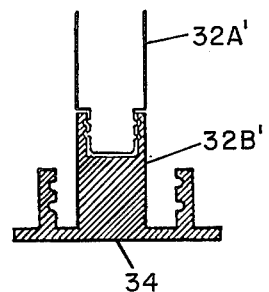
FIG. 1a is a longitudinal cross sectional view showing a modification of the piston arrangement.

Alternatively, the rod 32 may be composed of portion 32A' and 32B' which are threadedly connected together as shown in FIG. 1a. In any event, the main objective is that the portion 32B does not extend much beyond the closure member 20 as shown in FIG. 3 in order to obviate sealing or shipping problems.

With the closure member 20 in situ and in locking engagement with the piston 34, the rearward end is securely tightened for liquid integrity. The cap at this time either has already been or may then be secured to the forward end thereof in a manner as will be apparent from the preceding description.

In the assembled condition, as shown in FIG. 3, the syringe is now a liquid-tight storage container and can be shipped, for instance to a laboratory, for analysis. In preparation for inserting the syringe or attaching the syringe to a centrifuge (not shown), the members 20 and 34 are removed while cap 40 remains mounted on the nozzle 16. The vial 10 is then handled in the conventional manner for purposes of specimen analysis.

While there have been described what are at present considered to be the preferred embodiments of this invention, it will be obvious to those skilled in the art that various changes and modifications may be made therein without departing from the invention, and it is aimed, therefore, in the appended claims to cover all such changes and modifications as fall within the true spirit and scope of the invention.

What is claimed is:

1. Multi-purpose syringe for extracting a specimen, storing and shipping same and adapted to be employed as a test vial for centrifugation, comprising in combination:

a vial having a wall defining a tubular configuration and a forward and a rearward opening in communication with the interior of the vial;

a nozzle enclosing the forward opening and providing a passageway therefrom adapted for receiving a hypodermic needle;

a cap detachably mounted on said nozzle for sealingly covering said nozzle and the passageway thereof;

an end closure detachably secured to the rearward end of the vial sealingly enclosing the rear opening, and connecting means on said closure extending forwardly into the vial radially spaced from said wall;

and longitudinally extending piston means projecting a rod through said end closure into the vial and terminating therein with a piston head, said piston head including rearwardly extending connecting means radially spaced from the vial wall, with the connecting means of said end closure when said piston head is in a rearward position whereby unintentional axial movement of the piston head in a forward direction is generally precluded.

2. Multi-purpose syringe according to claim 1, wherein said rod has a first and second portion separable from each other.

3. Multi-purpose syringe according to claim 2, wherein the length of the first portion is significantly shorter than that of said second portion.

4. Multi-purpose syringe according to claim 3, wherein the juncture between the first and second portions is radially reduced to permit the second portion to be manually broken off at a predetermined location.

5. Multi-purpose syringe according to claim 3, wherein the rearward end of said first portion does not significantly protrude beyond the vial when the connecting means of the piston means and the end closure are in locking engagement.

6. Multi-purpose syringe according to claim 3, wherein the first and second portions are threadedly connected.

7. Multi-purpose syringe according to claim 2, and a manual grip on the rearward end of the second portion.

8. Multi-purpose syringe according to claim 1, wherein the piston head connecting means includes a tubular extension having an inner thread; and said end closure connecting means includes a tubular extension in sealing engagement with said rod and provided with an outer thread for meshing with the first mentioned thread.

* * * * *